(12) United States Patent
Gardeski et al.

(10) Patent No.: US 9,067,042 B2
(45) Date of Patent: Jun. 30, 2015

(54) STEERABLE STYLET WITH GUIDEWIRE TIP

(75) Inventors: Kenneth C. Gardeski, Plymouth, MN (US); Ronald A. Drake, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 869 days.

(21) Appl. No.: 12/771,265

(22) Filed: Apr. 30, 2010

(65) Prior Publication Data

US 2011/0270169 A1 Nov. 3, 2011

(51) Int. Cl.
*A61M 25/01* (2006.01)

(52) U.S. Cl.
CPC ... *A61M 25/0138* (2013.01); *A61M 2025/0161* (2013.01); *A61M 25/0147* (2013.01); *A61M 25/0133* (2013.01); *A61M 25/0136* (2013.01)

(58) Field of Classification Search
CPC .................... A61M 25/0133; A61M 25/0136; A61M 25/0138; A61M 25/0141; A61M 25/0144; A61M 25/0147
USPC ............................ 604/95.01–95.05, 523–532
See application file for complete search history.

(56) References Cited

U.S. PATENT DOCUMENTS

| | | | |
|---|---|---|---|
| 4,136,703 A | 1/1979 | Wittkampf |
| 4,381,013 A | 4/1983 | Dutcher |
| 4,676,249 A | 6/1987 | Arenas et al. |
| 4,815,478 A | 3/1989 | Buchbinder et al. |
| 4,898,577 A | 2/1990 | Badger et al. |
| 4,940,062 A | 7/1990 | Hampton et al. |
| 5,040,543 A | 8/1991 | Badera et al. |
| 5,170,787 A | 12/1992 | Lindegren |
| 5,327,906 A | 7/1994 | Fideler |
| 5,439,006 A | 8/1995 | Brennen et al. |
| 5,545,200 A | 8/1996 | West et al. |
| 5,662,119 A | 9/1997 | Brennan et al. |
| 5,728,148 A | 3/1998 | Bostrom et al. |
| 6,027,462 A | 2/2000 | Greene et al. |
| 6,059,739 A | 5/2000 | Baumann |

(Continued)

*Primary Examiner* — Nathan R Price

(57) ABSTRACT

According to an embodiment of the present invention, a steerable elongated medical device includes an outer tube extending between an outer tube proximal segment and an outer tube distal segment, and having an outer tube wall forming an outer tube lumen and an elongated outer tube slot through the outer tube wall to the outer tube lumen. The elongated outer tube slot has a first portion and a second portion and is formed between an outer tube slot proximal end and an outer tube slot distal end and extends axially along the outer tube distal segment through an outer tube slot length to define a cutaway portion of the outer tube. A reinforcing sleeve is positioned within the outer tube lumen and extends between a reinforcing sleeve proximal end and a reinforcing sleeve distal end. The reinforcing sleeve forms a reinforcing sleeve slot portion aligned with and extending along the first portion of the outer tube slot and includes a reinforcing sleeve overlap portion extending over the second portion of the outer tube slot. A handle is coupled to the outer tube proximal end, and a pull wire is positioned within the outer tube lumen and extends between a pull wire proximal end coupled to the handle and a pull wire distal end comprising a guidewire tip. The pull wire extends through the reinforcing sleeve lumen, the outer tube lumen, and a distal pull wire stop, and the guidewire tip extending distally from the distal pull wire stop and the pull wire proximal end is adapted to be manipulated to separate the pull wire proximal end from the outer tube proximal end to induce a bend in the cutaway portion.

11 Claims, 4 Drawing Sheets

(56) References Cited

U.S. PATENT DOCUMENTS

| | | |
|---|---|---|
| 6,146,338 A | 11/2000 | Gardeski et al. |
| 6,251,092 B1 | 6/2001 | Qin et al. |
| 6,280,433 B1 | 8/2001 | McIvor et al. |
| 6,379,346 B1 | 4/2002 | McIvor et al. |
| 7,101,361 B2 | 9/2006 | Gardeski |
| 2002/0013547 A1* | 1/2002 | Paskar .................. 604/95.04 |
| 2004/0116878 A1 | 6/2004 | Byrd et al. |
| 2004/0193037 A1* | 9/2004 | Tsukada et al. ............ 600/409 |

* cited by examiner

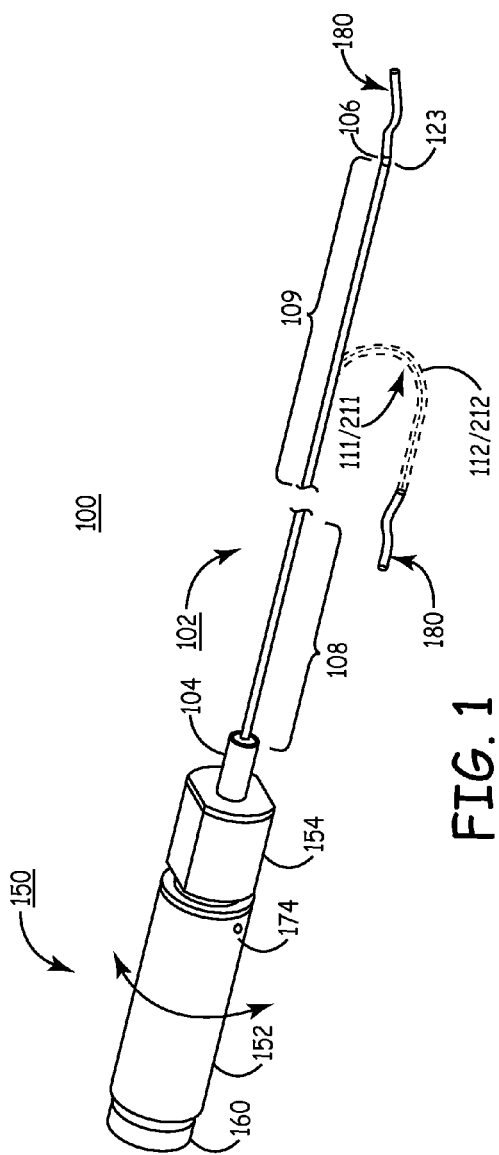
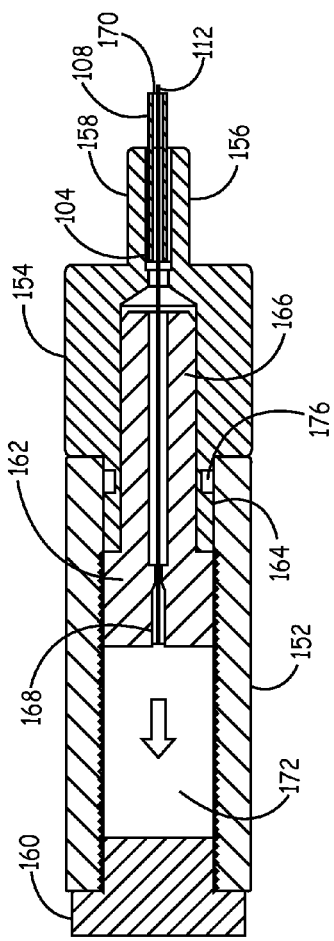

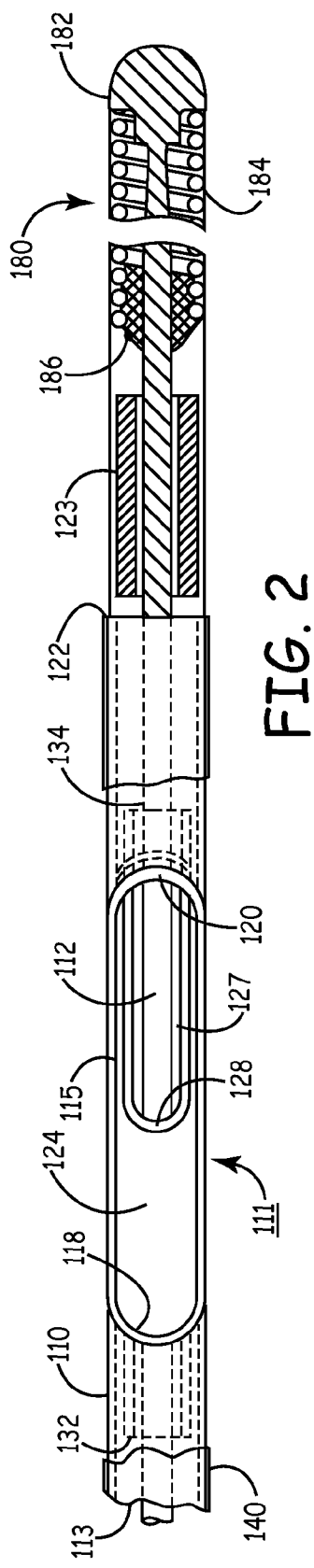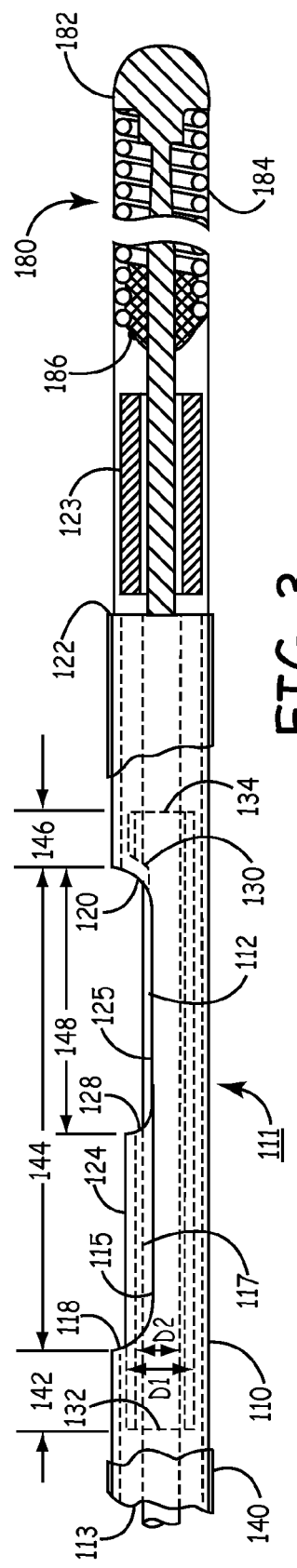

STEERABLE STYLET WITH GUIDEWIRE TIP

FIELD

The present invention pertains to use of elongated medical instruments to access a site in the body to facilitate introduction of a further medical device, and particularly to elongated steerable medical devices, such as a steerable stylets, for steering the distal end and imparting curves in distal segments of such medical instruments to facilitate implantation of a medical device.

BACKGROUND

A wide variety of elongated medical instruments are currently available that are adapted to be permanently or temporarily implanted in the mammalian body, usually the body of a human patient, or used to access a site in the body to facilitate introduction of a further implantable medical device or delivery of a therapeutic or diagnostic agent. Such elongated medical instruments have an instrument body extending between instrument body proximal and distal ends, and a distal segment of the instrument body is advanced to a remote site in the body.

In many cases, the introduction of such elongated medical instruments to a remote site in the body is effected through a skin incision accessing an incision into a blood vessel, whereby the instrument body is advanced through a pathway until the distal segment or the instrument body distal end are located at the remote site. Such advancement is often through a tortuous pathway having twists and turns requiring the capability to impart a curve or deflect the instrument body distal end to facilitate advancement. Therefore, the introduction of such elongated medical instruments through vascular pathways or other tortuous pathways in the body is facilitated by a wide variety of techniques and mechanisms that have been developed to impart curves in the distal segment of the instrument body or to deflect or steer the instrument body distal end.

There is still a perceived need for a steerable stylet having a small diameter stylet body that is simple and inexpensive to manufacture, resists kinking, and that can be manipulated to control the deflection of and impart a bend in a distal segment of the stylet body that is more acute.

SUMMARY

In one embodiment, the invention provides a steerable elongated medical device, that comprises an outer tube extending between an outer tube proximal end and an outer tube proximal end, having an outer tube wall forming an outer tube lumen and an elongated outer tube slot through the outer tube wall to the outer tube lumen, the elongated outer tube slot having a first portion and a second portion and formed between an outer tube slot proximal end and an outer tube slot distal end and extending axially along the outer tube proximal end through an outer tube slot length to define a cutaway portion of the outer tube, a reinforcing sleeve positioned within the outer tube lumen and extending between a reinforcing sleeve proximal end and a reinforcing sleeve distal end, wherein the reinforcing sleeve forms a reinforcing sleeve slot portion aligned with and extending along the first portion of the outer tube slot and includes a reinforcing sleeve overlap portion extending over the second portion of the outer tube slot, a handle coupled to the outer tube proximal end; and a pull wire positioned within the outer tube lumen and extending between a pull wire proximal end coupled to the handle and a pull wire distal end comprising a guidewire tip, the pull wire extending through the reinforcing sleeve lumen, the outer tube lumen, and a distal pull wire stop, and the guidewire tip extending distally from the distal pull wire stop, wherein the pull wire proximal end is adapted to be manipulated to separate the pull wire proximal end from the outer tube proximal end to induce a bend in the cutaway portion.

In another aspect, the invention provides a method of anchoring a steerable elongated medical device within a vessel. The method comprises guiding a distal portion of a steerable elongated medical device as described in this application to a desired site within a vessel within a vasculature and inducing a bend in the cutaway portion of the medical device, an outer tube wall opposite the cutaway portion being pressed against a vessel wall, and the pull wire distal end comprising a guidewire tip being pressed against an opposing vessel wall.

BRIEF DESCRIPTION OF THE DRAWINGS

FIG. 1 is a simplified perspective view of a steerable stylet in which the present invention can be incorporated;

FIG. 2 is a simplified top view of a distal segment of a stylet body having an elongated outer tube slot reinforced with an inner reinforcement sleeve and a guidewire tip;

FIG. 3 is a simplified side view of the distal segment of the stylet body of FIG. 2;

FIG. 4 is a cross-section view taken of an embodiment of stylet handle shown in FIG. 1;

DETAILED DESCRIPTION

Figure 5:
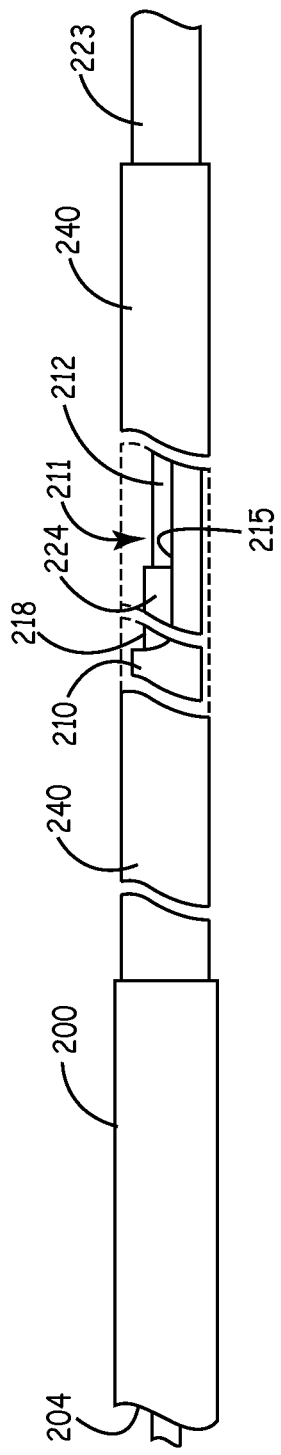
FIG. 5 is a simplified side view of a distal segment of a stylet body having an elongated outer tube slot reinforced with an inner reinforcement sleeve in accordance with a second embodiment of the present invention.

In the following detailed description, references are made to illustrative embodiments for carrying out the invention. It is understood that other embodiments may be utilized without departing from the scope of the invention. Although the present invention is described as preferably being applied to a steerable stylet, the aspects of the present invention are not intended to be limited to use in steerable stylets. Rather, it is understood that the present invention could be utilized in elongated medical devices other than steerable stylets, such as sheaths or catheters, for example. Embodiments of the steerable stylets of the present invention can be employed within the lumens of endocardial cardiac leads, particularly endocardial pacing and/or cardioversion/defibrillation leads, but it will be understood that the steerable stylets of present invention can be utilized in any elongated medical instruments of the types described or mentioned herein and equivalents that may presently exist or come into existence in the future.

Moreover, the steerable stylets of the present invention can advantageously be fabricated in a relatively large diameter for use in directing introducers or guide catheters through tortuous pathways, for example, for implanting cardiac leads that do not have lead lumens. Steerable stylet bodies for insertion into cardiac lead lumens typically have a stylet body outer diameter of about 0.016 inches. Larger diameter steerable stylets having an outer diameter of 0.022 inches, for example, (incorporating the reinforcing sleeve construction of the present invention) can advantageously be employed in guide lumens of such bilumen catheters having a guide lumen diameter exceeding the typical cardiac lead body lumen diameter. It is not easier to create more robust steerable stylets or medical devices that form smaller radii bends in the bendable distal sections of larger diameter (e.g., 0.022 inches) steerable stylet bodies than in smaller diameter (e.g., 0.016 inches) steerable stylets. Moreover, the larger diameter steerable stylet has sufficient torqueability to increase torqueability of certain guide catheter shafts or bodies or to impart torqueability to a guide catheter shaft or body lacking any torqueability. In addition, it is inherently easier and less expensive to fabricate such larger diameter steerable stylet bodies insertable into a guide lumen of a catheter body than to fabricate smaller diameter steerable stylets providing the same performance.

According to one embodiment, an elongated medical instrument, such as a steerable stylet 100, that includes a handle 150 and an elongated stylet body 102 in which embodiments and features of the present invention can advantageously be combined in various combinations is depicted in FIG. 1. The stylet body 102 extends a predetermined length between a stylet body proximal end 104 coupled to handle 150 and a stylet body distal end 106. The stylet body 102 further includes a stylet body proximal segment 108 and a stylet body distal segment 109. The stylet body 102 encloses an elongated pull wire 112 extending between a pull wire proximal end coupled to handle 150 and a pull wire distal end affixed to the pull wire stop 123 and to the guidewire head 182 of the guidewire tip 180, shown in detail in FIG. 2.

As shown in FIG. 1, the stylet handle 150 includes a proximal handle portion 152 and a distal handle portion 154 where proximal handle portion 152 rotates relative to distal handle portion 154 to induce a bend in the stylet body distal segment 109. For example, the pull wire proximal end is coupled to the handle insert 162 (shown in FIG. 4) and the stylet body proximal end 104 is coupled to the distal handle portion 154. The pull wire extends distally to a pull wire distal end that is coupled with the guidewire head 182 (FIG. 2).

The proximal handle portion 152 can be rotated and causes the pull wire attached to the handle insert 162 to be tensioned (but not twisted), and a bend, e.g., the 180° or greater bend depicted in broken lines depicted in FIG. 1, can be induced in the stylet body distal segment 109 in a plane defined by the cutaway or slot portion 111. While the term "pull wire" is used herein, it can be seen that in practice, the stylet body proximal end is pushed away from the pull wire proximal end. The induced bend remains even if the grip on the proximal and distal handle portions 152 and 154 is released.

One embodiment of the stylet body 102 is depicted in FIGS. 2 and 3. In this embodiment, an outer tube 110 extends the full length of the stylet body 102 through the proximal and distal segments 108 and 109 to an outer tube distal end 122. The outer tube 110 is preferably formed of stainless steel hypodermic needle or "hypotube" or a shape memory alloy, e.g., NITi alloy or NITINOL brand alloy, having an outer diameter of about 0.022 inches and an outer tube wall thickness of about 0.005 inches, providing an outer tube lumen 113 having an outer tube lumen diameter of about 0.012 inches.

An elongated portion of the outer tube wall is cut away through an arc of 180° along a cutaway portion 111 near the stylet body distal end between outer tube slot proximal end 118 and outer tube slot distal end 120 to form an elongated outer tube slot 115, for example, by grinding or EDM techniques. A reinforcement tube or sleeve 124 is fitted into the outer tube lumen 113 extending at least partly through the length of the outer tube slot 115. The reinforcement sleeve 124 has a reinforcement sleeve length extending between a reinforcement sleeve proximal end 132 and a reinforcement sleeve distal end 134, the length of the reinforcement sleeve 124 exceeding the length of the outer tube slot 115. The reinforcement sleeve 124, which is preferably formed of a shape memory alloy, forms a reinforcing sleeve lumen 127 so that reinforcing sleeve 124 has an outer diameter D1 of approximately 0.011 inches, for example, to fit the dimensions of the outer tube lumen 113, and an inner diameter D2 of approximately 0.008 inches, for example.

The reinforcement sleeve 124 is fitted into the outer tube lumen 113 so that a reinforcement sleeve proximal segment 142 extends proximally within outer tube lumen 113 from the proximal end 118 of the outer tube slot 115 and a reinforcement sleeve distal segment 146 extends distally within the outer tube lumen 113 from the distal end 120 of the outer tube slot 115. An elongated reinforcement sleeve intermediate segment 144 therefore extends the length of the outer tube slot 115. At least a portion 148 of the reinforcement sleeve intermediate segment 144 is cut away through 180° to form an elongated reinforcement sleeve slot 125 extending between reinforcement sleeve slot proximal end 128 and reinforcement sleeve slot distal end 130. The outer tube slot 115 and the reinforcement sleeve slot 125 are aligned, and the reinforcement sleeve proximal segment 142 is adhered to the wall of the outer tube lumen 113 to maintain the alignment. The adhesion can be effected employing epoxy adhesive, for example those sold under the tradename "HYSOL". The adhesion of the reinforcement sleeve proximal segment 142 to the wall of the outer tube lumen 113 allows the reinforcement sleeve intermediate and distal segments 144 and 146 free to slide along a wall of the outer tube lumen 113 when a bend is induced along the cutaway portion 111, such as by applying tension to the pull wire, for example. An overlap portion 117 of the reinforcement sleeve proximal to the reinforcement sleeve slot proximal end 128 and that extends within the outer tube slot 115 between reinforcement sleeve slot proximal end 128 and outer tube slot proximal end 118, provides strain relief bridging the outer tube slot proximal end 118 where buckling would otherwise likely take place.

In one example, the length of the reinforcement sleeve proximal segment 142 is approximately 0.100 inches, the length of the reinforcement sleeve intermediate segment 144 is approximately 0.750 inches, and the length of the reinforcement sleeve distal segment 146 is approximately 0.050 inches. The length of the reinforcement sleeve slot 125 is approximately 0.300 inches. The reinforcement sleeve distal end 134 is, at a minimum, approximately 0.100 inches from the outer tube distal end 122. The length dimensions and ratio of the length of the reinforcement sleeve slot 125 to the length of the reinforcement sleeve intermediate segment 144 and the outer tube slot 115 are be dependent upon the outer diameters, wall thicknesses, and materials of the outer tube and the reinforcement sleeve.

The ratio of the lengths of the solid wall reinforcement sleeve segments 142 and 146 and the ratio of the cut away reinforcement sleeve segment 148 with respect to the length of the outer tube slot 115 provide the optimal bending characteristics and resistance to kinking along the length of the outer tube slot 115. Stylet bodies having varying flexibility and possible shapes formed in the distal segments thereof can be achieved by controlling the dimensions of the outer tube slot 115 and the reinforcement sleeve slot 125. Generally, longer and deeper dimensions of the slots 115 and 125 increase flexibility but reduce rigidity in the cutaway portion 111. Thus, the dimensions of the slots 115 and 125 may be adjusted to provide the desired flexibility and rigidity of the cutaway portion 111 for the intended use.

In the illustrated embodiment, the slots 115 and 125 are shown to extend around the periphery of the outer tube 110 and the reinforcement sleeve 124 in an about 180° arc leaving intact arcuate tube walls of the outer tube 110 and reinforcement tube 124. The arc of the arcuate tube walls of the outer tube 110 and reinforcement tube 124 can differ from 180° and can differ from one another to achieve the desired flexibility and resulting bend shape.

The pull wire 112 extends through the reinforcement sleeve lumen 127 and the outer tube lumen 113 through a cylindrical pull wire stop 123 and a distal end comprising a guidewire tip 180. The pull wire stop 123 is in the form of a crimp sleeve in this embodiment. A portion of pull wire 112 proximate the guidewire tip 180 and distal the outer tube distal end 122 is crimped into a lumen of the pull wire stop 123. The cylindrical distal pull wire stop 123 has an outer diameter approximately equal to the diameter of the outer tube 120, so that the cylindrical distal pull wire stop 123 bears against the outer tube distal end 122 when stressed. In this way, the pull wire distal end is also "coupled" to the outer tube distal end 122 as well as the guidewire tip 180 as indicated in FIG. 2.

Figure 6:
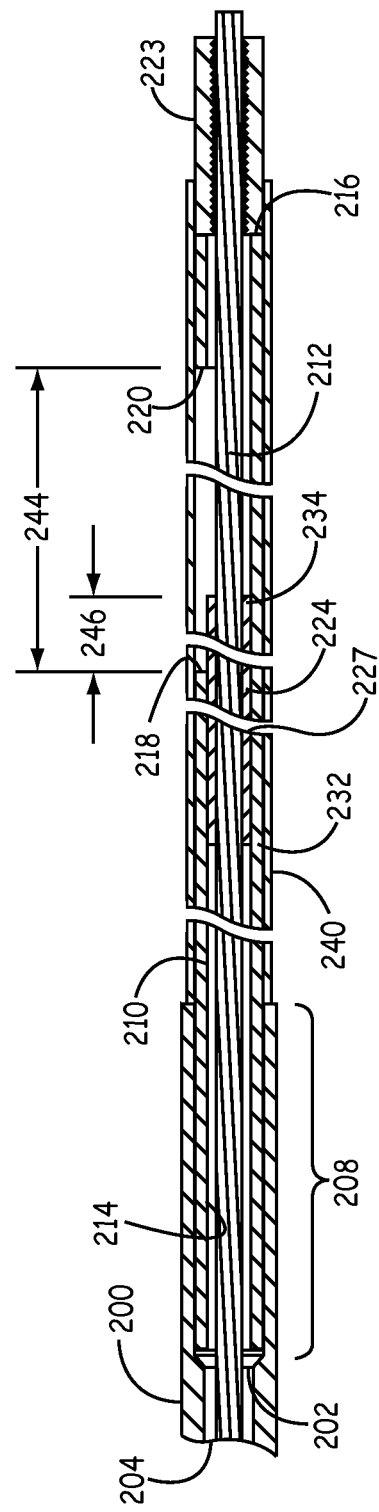
FIG. 6 is a cross-sectional view of the distal segment depicted in FIG. 5.

Optionally, the pull wire 112 can be formed having a taper along its length, whereby the pull wire diameter extending through the aligned outer tube slot 115 and reinforcement sleeve slot 125 is less than the pull wire diameter proximal to the aligned outer tube slot 115 and reinforcement sleeve slot 125. For example, the pull wire 112 can have a proximal wire diameter of 0.005 to 0.008 inches that is tapered to a distal wire diameter of 0.0025 inches. In this embodiment, the diameter of the pull wire ranges from about 0.005 to about 0.008 inches. Desirably, the taper of the wire begins before the junction 208 as shown in FIG. 6.

In one embodiment, guidewire tip 180 comprises a guidewire head 182 attached to the distal end of the pull wire and a coiled wire 184, for example, platinum wire that abuts the guidewire head and is attached to the guidewire via an epoxy adhesive 186. The length of the guidewire tip 180 can range from about 8 to about 35 mm. In other embodiments, the length of the guidewire tip can range from 10 to 25 mm, and any range or any length between such range.

The guidewire head is typically radiopaque. One example of a radiopaque guidewire head is one made from an alloy of platinum iridium.

The pull wire stop 123 can have a length that ranges from about 1 mm to about 5 mm, and any range or any length between such range.

The total length of the pull wire distal from the outer tube distal end 122 (the length of the pull wire stop 123 plus the length of the guidewire tip 180) ranges from 9 mm to 40 mm, and any range or any length between such range.

The length of pull wire between the pull wire stop 123 and the guidewire tip 180 can range from 4 mm to 39 mm. The guidewire and guidewire tip distal from the pull wire stop 123 typically is more flexible than the medical device proximal 108 and distal 109 segments.

The shortened length of the cutaway portion 111 achieved by use of the reinforcement sleeve 124 also shortens the exposed length of the pull wire 112 so that it cannot extend as far away from the outer tube 110 when the outer tube 110 bows outward upon tensioning of the pull wire 112. Optionally, a polymeric outer sleeve 140 is fitted over the outer tube 110 to extend over the aligned outer tube slot 115 and reinforcement sleeve slot 125 to retain the pull wire 112 generally within the reinforcement sleeve lumen 127 when the pull wire 112 is retracted to form a bend in the nested outer tube and reinforcement sleeve walls. The polymeric outer sleeve 140 is formed of polyimide or PEEK, for example, that is fitted or adhered over the outer tube 110.

In these ways, the reinforcement sleeve 124 reinforces the wall of the outer tube 110 through at least a portion of the length of the outer tube slot 115 to prevent buckling when a bend is induced in the outer tube 110 and the reinforcement sleeve 124. In this way, when the elongated medical instrument includes a pull wire, a bend can be safely induced in the remaining arcuate section of the outer tube wall when the pull wire 112 extending through the outer tube lumen 113 is retracted with respect to the outer tube 110 (or the outer tube 110 is pushed distally with respect to the pull wire 112) by manipulation of the handle 150.

Referring again to FIG. 1, it is also possible to employ the principles of the present invention in a distal segment 109 of a stylet body 102 that is formed differently than the proximal segment 108 (or an intermediate segment) of the stylet body 102. The outer tube 110 can be replaced by a proximal outer tube segment and a distal outer tube segment formed of the same or differing materials, and having the same or differing wall outer tube diameters, wall thicknesses, and bending characteristics. The proximal and distal outer tube segments are joined together end-to-end, and the outer tube slot is formed in the tube wall of the distal tube segment.

For example, the proximal segment 108 of stylet body 102 can be formed from a proximal outer tube of stainless steel, e.g., 304W stainless steel alloy that is joined at a junction with a distal outer tube 110 that is formed of a shape memory alloy, e.g., NITINOL. In another embodiment, the proximal segment 108 can be formed of a wire braid reinforced polymer tube.

In the embodiment depicted in FIGS. 5 and 6, the junction 208 is effected by an elongated distal counterbore 202 of the tube wall of the proximal outer tube 200 formed of stainless steel into which a proximal segment of the distal outer tube 210 is fitted and adhered employing epoxy cement or the like. A proximal outer tube lumen 204 is thereby axially aligned with a distal outer tube lumen 214. The proximal outer tube 200 preferably has an outer diameter of nominally 0.022 inches and an outer tube wall thickness of nominally 0.005 inches, providing an outer tube lumen 204 having a nominal outer tube lumen diameter of 0.012 inches. The counterbore diameter is preferably nominally 0.017 inches to receive a distal outer tube 210 having an outer diameter of nominally 0.016 inches and a distal outer tube lumen nominal diameter of 0.011 inches.

An elongated portion of the distal outer tube wall is cut away through 180° near the stylet body distal end between distal outer tube slot proximal end 218 and distal outer tube slot distal end 220 to form an elongated outer tube slot 215. Thus, an intact proximal tubular portion of the distal outer tube 210 extends proximally from the distal outer tube slot proximal end 218, and an intact distal tubular portion of the distal outer tube 210 extends distally from distal outer tube slot distal end 220.

A tubular distal reinforcement tube or sleeve 224 is fitted into the distal outer tube lumen 214 extending at least partly through the length of the distal outer tube slot 215. The reinforcement sleeve 224 is preferably formed of a shape memory alloy and has an outer sleeve outer diameter of 0.016 inches, for example, and a reinforcement sleeve lumen 227 inner sleeve lumen diameter of 0.105 inches, for example.

The reinforcement sleeve 224 has a reinforcement sleeve length extending between a reinforcement sleeve proximal end 232 and a reinforcement sleeve distal end 234. In this embodiment, the reinforcement sleeve 224 is tubular and does not have an elongated slot cut away leaving an arcuate section of the tubular wall. And, the reinforcement sleeve 224 does not exceed the length of the outer tube slot 215, whereby the reinforcement sleeve distal end 234 is disposed intermediate the distal outer tube slot proximal end 218 and distal outer tube slot distal end 220. For example, the distal outer tube slot 215 can have a nominal length of 1.500 inches, and the reinforcement sleeve distal end 234 is disposed nominally at 0.375 to 0.750 inches from the distal outer tube slot proximal end 218 and distal outer tube slot distal end 220.

The pull wire 212 extends through the reinforcement sleeve lumen 227, the distal outer sleeve lumen 214 and the proximal outer sleeve lumen 204 to a cylindrical distal pull wire stop 223. The distal end of the pull wire 212 is crimped into a lumen of the distal pull wire stop 223. The cylindrical distal pull wire stop 223 has an outer diameter that exceeds the distal outer tube lumen 214 and bears against the distal outer tube distal end 216 when stressed.

Optionally, the pull wire 212 can be formed having a taper along its length, whereby the pull wire diameter extending through the distal outer tube slot 215 and reinforcement sleeve lumen 227 is less than the pull wire diameter within the proximal outer tube lumen 204. For example, the pull wire 212 can have a proximal wire diameter of 0.010 inches that is tapered to a distal wire diameter of 0.006 inches.

Optionally, a polymeric outer sleeve 240 is fitted over the distal outer tube 210 to extend over the aligned distal outer tube slot 215 and the reinforcement sleeve 224 to retain the pull wire 212 generally within the distal outer tube lumen 214 when the pull wire 212 is retracted to form a bend in the distal outer tube 210 and the reinforcement sleeve 224 in the cutaway portion 211. The polymeric outer sleeve 240 can comprise polyimide or PEEK that is fitted or adhered over the outer tube 210.

In these ways, the reinforcement sleeve 224 reinforces the wall of the distal outer tube 210 across the outer tube slot proximal end 218 and through at least a portion 246 of the full length 244 of the distal outer tube slot 215 to prevent buckling when a bend is induced in the distal outer tube 210 and the reinforcement sleeve 224 in the cutaway portion 211. A bend can be safely induced in the arcuate section of the distal outer tube wall when the pull wire 212 extending through the aligned lumens is retracted with respect to the proximal and distal outer tubes 200 and 210 (or the outer tubes 200 and 210 are pushed distally with respect to the pull wire 212) by manipulation of handle 150.

Again, the characteristics of the induced bend can be altered by the selection of the length 244 of the cutaway portion 211, and the ratio of the segment length 246 to the full length 244 of the cutaway portion 211. It should be noted that the reinforcement sleeve 224 can be shaped in the same manner as slotted reinforcement sleeve 124 described above with respect to FIGS. 2 and 3. Additionally, reinforcement sleeve 124, 224 may also be comprised of a wire coil, for example, such as the coil described in U.S. Pat. No. 6,146,338, incorporated by reference in this application for the description of a coil.

Referring again to FIG. 1, the stylet handle 150 can take any form that enables the application of tension between and to separate the proximal end of the pull wire 112 and the stylet body proximal end 104 apart to steer the stylet body distal end 106 and induce a bend along the cutaway portion 111.

A particular configuration of the stylet handle 150 is shown in FIG. 4. The distal handle portion 154 has a tubular distal projection 156 into which the stylet body 104 is inserted and attached by adhesive. A distal handle portion lumen 158 extends through the distal handle portion 154. The proximal handle portion 152 is tubular and threaded internally within proximal handle portion lumen 172 at its proximal end to receive a handle end cap 160 and threaded more distally to receive the threads on the distal projection 168 of a handle insert 162 to enable the handle insert 162 to be moved distally to release tension or proximally to increase tension on the pull wire 112. The proximal end opening of the proximal handle portion 152 receives a tubular proximal projection 164 of the distal handle portion 154. The handle insert 162 comprises a handle insert proximal projection 166 extending into the distal handle portion lumen 158 and a threaded handle insert distal projection 168 that is attached to the internal threads of the proximal handle portion 152. The pull wire 112 is inserted through a handle insert lumen 170 that is axially aligned with the distal handle portion lumen 158 extending through the tubular distal projection 156. The proximal end of the pull wire 112 is attached to the handle insert 162.

One side of the handle insert distal projection 166 is flattened and bears against a guide pin (not shown) extending across the proximal handle lumen 172. A groove 176 is formed around the tubular proximal projection 164 to track a further guide pin (not shown). The user grips the sides of the distal handle portion 154 and rotates the proximal handle portion 152 to rotate the internal screw threads around lumen 172 with respect to the mating screw threads around handle insert distal projection 168 to move handle insert 162 proximally. The proximal movement tensions the pull wire 112 and induces the bend 111 as described above. Advantageously, the handle 150 is light in weight, and the tension and induced bend remains in place even if the handle 150 is released so that the user can manipulate the guide catheter handle without having to focus on manually maintaining the bend.

The above-described steerable medical devices advantageously facilitate the direct implantation of elongated cardiac leads having stylet lumens or the introduction and steering of guide catheters to a site of implantation of such cardiac leads or other medical devices or therapeutic or diagnostic substances.

Figure 7:
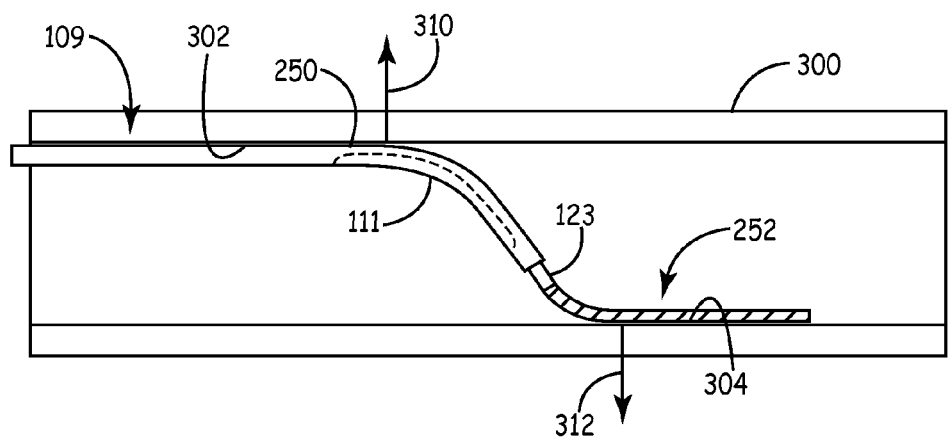
FIG. 7. is a depiction of an embodiment of the distal segment of a medical device of the invention anchored within a vessel.

For example, once the medical devices of the invention are guided to a desired site within a vasculature, such steerable medical devices can be anchored within a vessel. As shown in FIG. 7, the distal segment 109 can be anchored within a vessel 300 by inducing a bend along the cutaway portion 111. The outer tube wall of the outer tube opposite the cut away portion 250 is pressed against the vessel wall 302 by induced force depicted by arrow 310 while the bend along the cutaway portion 111 presses the guidewire portion 252 that is distal to the pull wire stop 123 against the opposing wall 304 of the vessel by an opposing induced force depicted by arrow 312. It is believed that the steerable medical devices described in this application may be anchored within vessels having a diameter of 3 mm or less.

While specific examples have been described in the specification and illustrated in the drawings, it will be understood by those of ordinary skill in the art that various changes may be made and equivalents may be substituted for elements thereof without departing from the scope of the present disclosure. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification but that the scope of the present disclosure will include any embodiments falling within the foregoing description.

The invention claimed is:

1. A steerable elongated medical device, comprising:
an outer tube extending between an outer tube proximal end and an outer tube distal end, having an outer tube wall forming an outer tube lumen and an elongated outer tube slot through the outer tube wall to the outer tube lumen, the elongated outer tube slot having a first portion and a second portion and formed between an outer tube slot proximal end and an outer tube slot distal end and extending axially along the outer tube proximal end through an outer tube slot length to define a cutaway portion of the outer tube;
a reinforcing sleeve positioned within the outer tube lumen and extending between a reinforcing sleeve proximal end and a reinforcing sleeve distal end, wherein the reinforcing sleeve forms a reinforcing sleeve slot portion aligned with and extending along the first portion of the outer tube slot and includes a reinforcing sleeve overlap portion extending over the second portion of the outer tube slot;
a handle coupled to the outer tube proximal end; and
a unitary pull wire positioned within the outer tube lumen and extending between a pull wire proximal end coupled to the handle and a pull wire distal end terminating at a guidewire head of a guidewire tip, the pull wire extending through the reinforcing sleeve lumen, the outer tube lumen, and a distal pull wire stop, and the guidewire tip extending distally from the distal pull wire stop, wherein the pull wire proximal end is adapted to be manipulated to separate the pull wire proximal end from the outer tube proximal end to induce a bend in the cutaway portion, wherein the guidewire tip has a flexibility that is greater than the flexibility of the medical device between the outer tube proximal and distal ends, and wherein a distal portion of the steerable medical device includes the cutaway portion and the guidewire tip, the distal portion capable of being induced to form a reverse compound curve at a site within a vasculature, the medical device having no preformed curves.

2. The device of claim 1 further comprising a polymeric outer sleeve fitted over the outer tube extending over the aligned outer tube slot and reinforcing sleeve slot portion and the reinforcing sleeve overlap portion to retain the pull wire when the pull wire is retracted to form a bend in the cutaway portion.

3. The device of claim 1, wherein the outer tube wall is cut away through an arc of approximately 180° to form the outer tube slot.

4. The device of claim 1, wherein the reinforcing sleeve is formed of a shape memory alloy.

5. The device of claim 1, wherein the device is insertable within a bilumen guide catheter having a guide lumen for receiving the device and a delivery lumen for receiving an elongated electrical medical lead body for implantation at a cardiac site.

6. The device of claim 1 wherein the pull wire has a length that extends distal from the outer tube distal end and the length is from 9 mm to 40 mm.

7. The device of claim 1 wherein the guidewire tip comprises a radiopaque guidewire head.

8. The device of claim 1 wherein the pull wire has a diameter and the diameter of the pull wire extending through the outer tube slot and the reinforcing sleeve slot is less than the diameter of the pull wire proximal to the outer tube slot and the reinforcing sleeve slot.

9. The device of claim 1 wherein the guidewire tip has a length of from about 8 mm to about 35 mm.

10. The device of claim 1 wherein the pull wire has a length between the pull wire stop and the guidewire tip of ranges from 4 mm to 39 mm.

11. A method of anchoring a steerable elongated medical device comprising:
guiding a distal portion of the steerable elongated medical device according to claim 1 to a site within a vasculature; and
inducing a bend in the cutaway portion of the medical device, an outer tube wall opposite the cutaway portion being pressed against a vessel wall, and the pull wire distal end comprising a guidewire tip being pressed against an opposing vessel wall.

* * * * *